(12) United States Patent
Li et al.

(10) Patent No.: US 9,980,484 B2
(45) Date of Patent: May 29, 2018

(54) CHITOSAN BASED HIGH PERFORMANCE FILTER WITH SELF-REGENERATING ABILITY

(71) Applicant: Nano and Advanced Materials Institute Limited, Hong Kong (HK)

(72) Inventors: Jifan Li, Hong Kong (HK); Yee Man Ho, Hong Kong (HK); Ka Chun Lee, Hong Kong (HK); Wai Yan Chan, Hong Kong (HK); Mui Chan, Hong Kong (HK); Kai Ming Yeung, Hong Kong (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 491 days.

(21) Appl. No.: 14/501,059

(22) Filed: Sep. 30, 2014

(65) Prior Publication Data

US 2015/0018306 A1 Jan. 15, 2015

Related U.S. Application Data

(63) Continuation-in-part of application No. 13/741,368, filed on Jan. 14, 2013, now abandoned.

(Continued)

(51) Int. Cl.
*A01N 43/16* (2006.01)
*B01J 21/06* (2006.01)
(Continued)

(52) U.S. Cl.
CPC ......... *A01N 43/16* (2013.01); *B01D 39/1676* (2013.01); *B01J 20/267* (2013.01);
(Continued)

(58) Field of Classification Search
None
See application file for complete search history.

(56) References Cited

FOREIGN PATENT DOCUMENTS

| CN | 101210081 B | 8/2010 |
|---|---|---|
| CN | 103239941 A | 8/2013 |

(Continued)

OTHER PUBLICATIONS

Kim SE, Park JH, Cho YW, Chung H, Jeong SY, Lee EB, Kwon IC. Porous chitosan scaffold containing microspheres loaded with transforming growth factor-beta1: implications for cartilage tissue engineering. J Control Release. Sep. 4, 2003;91(3):365-74.*

(Continued)

*Primary Examiner* — Krishnan S Menon
*Assistant Examiner* — Eric J McCullough
(74) *Attorney, Agent, or Firm* — Spruson & Ferguson (Hong Kong) Limited

(57) ABSTRACT

A self-regenerating chitosan based filter medium for disinfecting and purifying organic pollutants and other pollutants in a gas or liquid is disclosed herein. Porosity and surface charge of said filter medium is manipulative/tunable by varying one or more of the following parameter(s): concentration of chitosan, crosslinking density, amount of copolymers and additives, freezing temperature, freezing profile, and/or types of crosslinker used. The present filter medium is capable of self-regenerating under exposure to ultra-violet light for sufficient time and removing over 90% of the pollutants from each influent flowing through the filter medium.

18 Claims, 10 Drawing Sheets

Related U.S. Application Data

(60) Provisional application No. 61/961,443, filed on Oct. 15, 2013.

(51) Int. Cl.
  B01J 20/30 (2006.01)
  B01J 20/28 (2006.01)
  B01J 20/26 (2006.01)
  B01D 39/16 (2006.01)

(52) U.S. Cl.
  CPC ... B01J 20/28083 (2013.01); B01J 20/28085 (2013.01); B01J 20/3085 (2013.01); B01J 21/063 (2013.01); B01D 2239/10 (2013.01)

(56) References Cited

FOREIGN PATENT DOCUMENTS

| JP | 02261838 A | * | 10/1990 | |
|---|---|---|---|---|
| WO | WO 2012109239 A1 | * | 8/2012 | ......... B29C 47/0004 |
| WO | 2014020132 A1 | | 2/2014 | |

OTHER PUBLICATIONS

Shu, X.z., and K.J. Zhu. "A Novel Approach to Prepare Tripolyphosphate/chitosan Complex Beads for Controlled Release Drug Delivery." International Journal of Pharmaceutics 201.1 (2000): 51-58.*

Suwanchawalit et al., Fabrication of ice-templated macroporous TiO2-chitosan scaffolds for photocatalytic applications, Journal of Materials Chemistry, 2009, 19, 8478-8483.*

Chang, B.S. and Patro, S.Y. 2004. Freeze-drying Process Development for Protein Pharmaceuticals. in "Lyophilization of Biopharmaceuticals" (Costantino, H.R. and Pikal, M.J. eds) American Association of Pharmaceutical Scientists. pp. 113-138.*

Hoven, V., V. Tangpasuthadol, Y. Angkitpaiboon, N. Vallapa, and S. Kiatkamjornwong. "Surface-charged Chitosan: Preparation and Protein Adsorption." Carbohydrate Polymers 68.1 (2007): 44-53.*

English Machine Translation of JP 02261838 A.*

H Dureja, A.K Tiwary, S Gupta, Simulation of skin permeability in chitosan membranes, International Journal of Pharmaceutics, vol. 213, Issue 1, 2001, pp. 193-198.*

Cheewita Suwanchawalit et al., Fabrication of ice-templated macroporous TiO2-chitosan scaffolds for photocatalytic applications, Journal of Materials Chemistry 19 (2009) 8478-8483.

Xin Zhang et al., Degradation characteristic of TiO2-chitosan adsorbent on Rhodamine B and purification of industrial wastewater, Korean Journal of Chemical Engineering 28(5) (2011) 1241-1246.

First Office Action with Search Report of CN201410545894.2 issued by the State Intellectual Property Office of China dated Nov. 4, 2015.

* cited by examiner

CHITOSAN BASED HIGH PERFORMANCE FILTER WITH SELF-REGENERATING ABILITY

CROSS REFERENCE TO RELATED APPLICATIONS

The present application is a continuation-in-part application of U.S. non-provisional patent application Ser. No. 13/741,368 filed Jan. 14, 2013 and also claims priority of US provisional patent application Ser. No. 61/961,443 filed Oct. 15, 2013, and the disclosure of which are incorporated herein by reference in their entirety.

FIELD OF THE INVENTION

The presently claimed invention relates to a high performance filter with self-regenerating ability, in particular, to a chitosan based high performance filter with self-regenerating ability, manipulative porosity, and tunable surface chargeability, in order to efficiently remove specific size of particulates, heavy metals, bacteria and organic pollutants from gases or liquid flowing therethrough.

BACKGROUND OF THE INVENTION

Chitosan, a polycationic biopolymer of (1-4)-linked 2-amino-2deoxy-D-glucopyranose, is an abundant natural polysaccharide, which is well known for the superb capacity to adsorb contaminants and heavy metals and kill the bacteria in gases and water. Thus it is a good candidate for fabricating a filtering medium to disinfect and purify the gases and water. However, most conventional filters are not self-regenerative and require replacement regularly after the filter is fully accumulated with contaminants. The pore size of conventional filter medium is also not readily manipulated to suit various particulates. Other problems such as fixed surface charge and low mechanical strength also need to be addressed in the present invention.

SUMMARY OF THE INVENTION

Accordingly, a self-regenerative and porosity manipulative chitosan based filter medium with tunable surface charge is provided in the presently claimed invention. In one embodiment, the pore size of the filter medium is manipulated by varying one or more of the following parameter(s): concentration of biopolymer such as chitosan, crosslinking density, amount of copolymers and additives, freezing speed and profile, and/or types of crosslinker used. The pore size of the present filter medium ranges from 100 nm to 100 µm. In another embodiment, surface charge of the filter medium is tuned by adding different agents to tune the surface and/or density of the chitosan. In yet another embodiment, the self-regenerative ability is introduced by incorporating an effective amount of photocatalytic materials such as metallic oxide including but not limited to titanium dioxide, zinc oxide, vanadium oxide, and manganese dioxide, which are in nanomized size, in order to restore the capacity of the filter medium effectively under light activation of certain wavelength while the photocatalytic materials can also decompose organic pollutants accumulated on the medium after the performance deteriorates. The photocatalytic materials to be incorporated into the presently claimed filter medium are in particle form with a particle size ranging from 10 nm to 10 µm. It is believed that the incorporation of photocatalytic materials into the present filter medium would reinforce the mechanical strength. The presently claimed filter medium further comprises chitosan derivatives, or a mixture of chitosan with polymers. In an embodiment, the weight ratio of chitosan to polymer is from 1:1 to 3:1, depending on the desired porosity to be made. Said polymer can be synthetic polymers such as polyvinyl alcohol (PVA), polyethylene glycol, and polyacrylic acid, or biopolymers such as cellulose, carrageenan, and alginate. Said chitosan derivatives can be in crosslinked form by reacting with a crosslinker or in an uncrosslinked form. The crosslinker used for crosslinking chitosan to form said crosslinked chitosan derivatives includes but not limited to Trisodium citrate dihydrate, sodium hydroxide, tripolyphosphate (TPP), glyoxal, glutaraldehyde, polyethylene glycol, epichlorohydrin, N-hydroxysuccinimide, 1-ethyl-3-(3-dimethylaminopropyl) carbodiimide, (1,4 butanediol diglycidyl ether), formaldehyde, genipin, and oxalic acid. In one embodiment, said crosslinker is in a concentration from 0.017M to 0.136M. Said polymer can be in a weight percentage from 0.24 wt % to 0.50 wt %. Freezing temperature is also critical to the morphology and pore size of the present filter medium. Said freezing temperature can be from −10° C. to −55° C. Freezing profile is preferably from room temperature to −50° C. gradually at about 1° C./min before the filter medium is air dried.

Chitosan in its original form adopts a positive charge which can attract negatively charged materials. However the surface chargeability and density of chitosan can be altered to suit the specific applications, which means that the surface of the chitosan based filtering medium can be positively charged, negatively charged, and neutralized. For example, the positively charged surface can remove the negatively charged pollutants from water, such as $E.\ Coli$ and Congo red. The negatively charged surface can bind the positively charged pollutants, such as $S.\ maltophilia$ and Methylene blue. The neutral surface is to filter off the particles by physically blocking them. In one embodiment, the surface of the chitosan based filter medium can be introduced with quaternary ammonium to carry positive charge. In another embodiment, 5-formyl-2-furansulfonic acid can be introduced into the chitosan based filter medium to carry negative charge. In yet another embodiment, the surface of the chitosan filtering medium can be neutralized by treating the chitosan based filter medium with sodium hydroxide solution.

The chitosan based filtering medium of the present invention can effectively remove the heavy metals, bacteria, and organic pollutants. For example, it can achieve more than 99% removal rate on $E.\ Coli$, more than 98 mg/g absorptibility on Cd, more than 78 mg/g absorptibility on Pb, more than 175 mg/g absorptibility on Hg, and more than 90% removal efficiency on the organic pollutant, such as Allura red and Congo red.

DETAILED DESCRIPTION OF THE INVENTION

Reference will now be made in detail to the presently preferred embodiment of the present invention, serve to explain the principles of the invention. These embodiments or examples are described in sufficient detail to enable those skilled in the art to practice the invention, and it is to be understood that other embodiments may be utilized, and that changes may be made without departing from the spirit of the present invention.

EXAMPLES

Example 1—Manipulating Pore Sizes By Adjusting Crosslinking Degree

Figure 1:
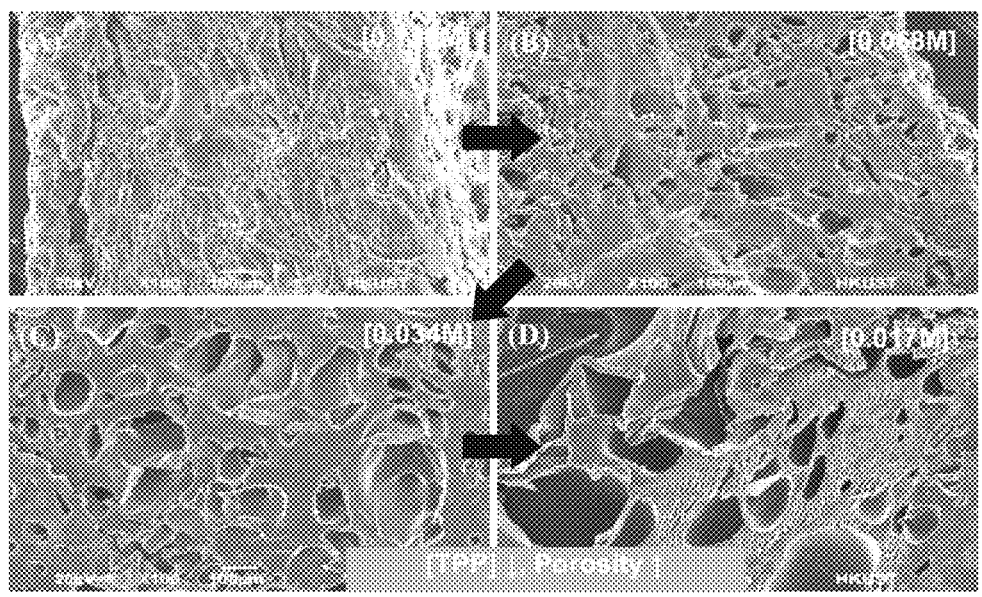
FIG. 1 shows SEM images of the porous chitosan based filter medium prepared by using different concentration of crosslinker: (A) 0.136M sodium tripolyphosphate (TPP); (B) 0.068M TTP; (C) 0.034M TTP; (D) 0.017M TTP.
Figure 2:
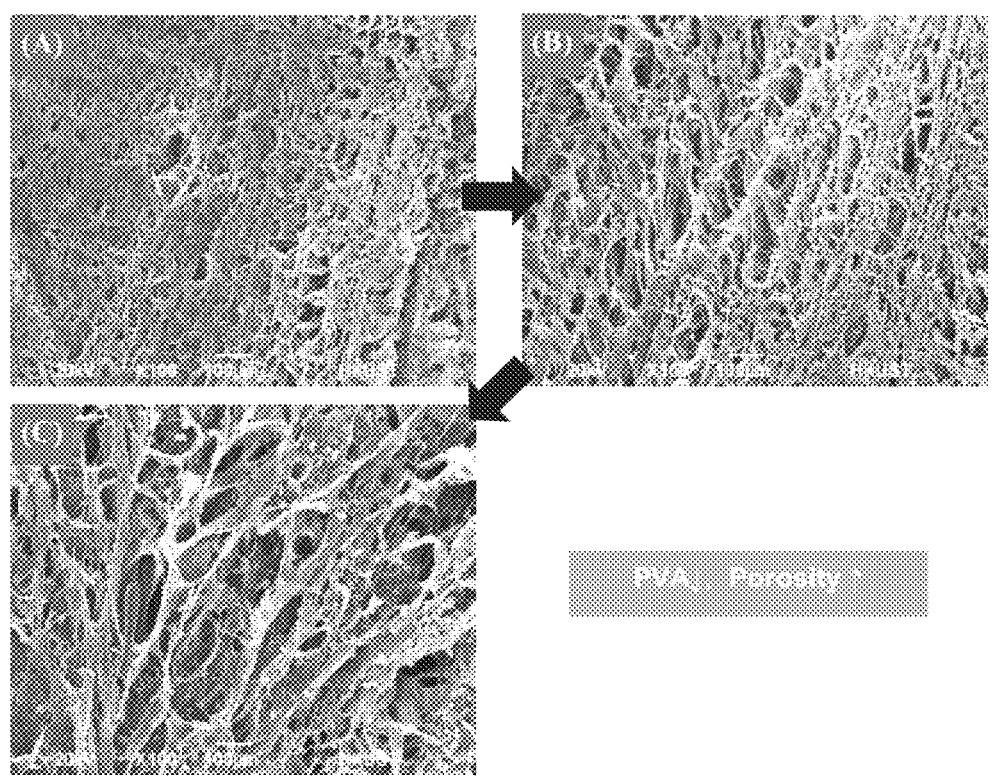
FIG. 2 shows SEM images of the porous chitosan based filter medium prepared by using different amount of PVA and chitosan: (A) 0.50 wt % PVA, 0.32 wt % chitosan; (B) 0.48 wt % of PVA, 0.45 wt % chitosan; (C) 0.24 wt % PVA, 0.61 wt % chitosan. TPP content is kept constant at 0.50 wt % among the three samples in this embodiment.

Sodium tripolyphosphate (TPP) is a non-toxic crosslinker used in the present invention to ionically crosslink the chitosan polymer. The amount of TPP added into the chitosan based filter medium has direct impact on the pore size of the filter medium. With the decrease of the TPP amount, the pore size of the chitosan based filter medium increases (FIG. 1). The pore size varies from a few microns to over 100 microns, preferably 5 microns. In this example, 1.8% w/w of chitosan is used.

Example 2—Manipulating Pore Sizes By Adjusting Copolymer Amount

In this example, the pore sizes of the chitosan scaffold can be fine tuned by adjusting the amount of copolymer added. For example, poly(vinyl alcohol) (PVA) is added into the chitosan scaffold to modify its morphology. With decrease of the amount of PVA, the pore size of the chitosan based filter medium increases. PVA is able to fill up the space among crosslinked chitosan so as to minimize the pore size. The range of the pore size can be from a few microns to several hundred microns, preferably 5 microns.

TABLE 1

The amount of PVA used in the chitosan membrane:

| Sample No. | PVA (wt %) | Chitosan (wt %) | TPP (wt %) |
|---|---|---|---|
| 1 | 0.50 | 0.32 | 0.50 |
| 2 | 0.48 | 0.45 | 0.50 |
| 3 | 0.24 | 0.61 | 0.50 |

Example 3—Manipulating Pore Sizes By Using Different Freezing Methods

Figure 3:
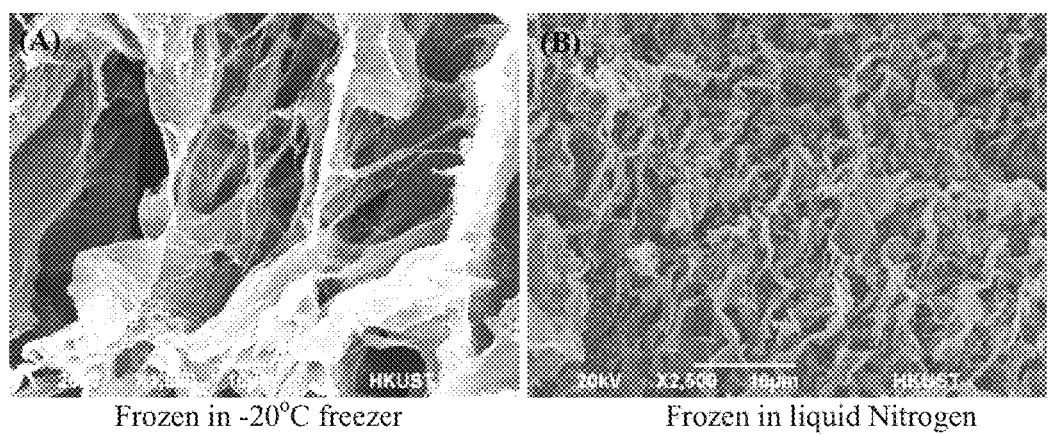
FIG. 3 shows SEM images of chitosan based filter medium prepared by using different freezing temperatures: (A) frozen at −20° C. freezer; (B) frozen at liquid nitrogen.

The chitosan solution needs to be frozen before freeze drying. The freezing method is one of the determining factors to control the pore size. Taking PVA/chitosan copolymer solution (Table 2) as an example, the chitosan membrane frozen in a normal −20° C. freezer (FIG. 3A) generates much larger pores than that being frozen in liquid nitrogen (about −210° C. to −196° C.) (FIG. 3B).

TABLE 2

The formula of PVA/Chitosan copolymer solution:

| PVA (wt %) | Chitosan (wt %) | TPP (wt %) |
|---|---|---|
| 0.50 | 0.32 | 0.50 |

Example 4—Manipulating Pore Sizes By Controlling Freezing Profile

Figure 4:
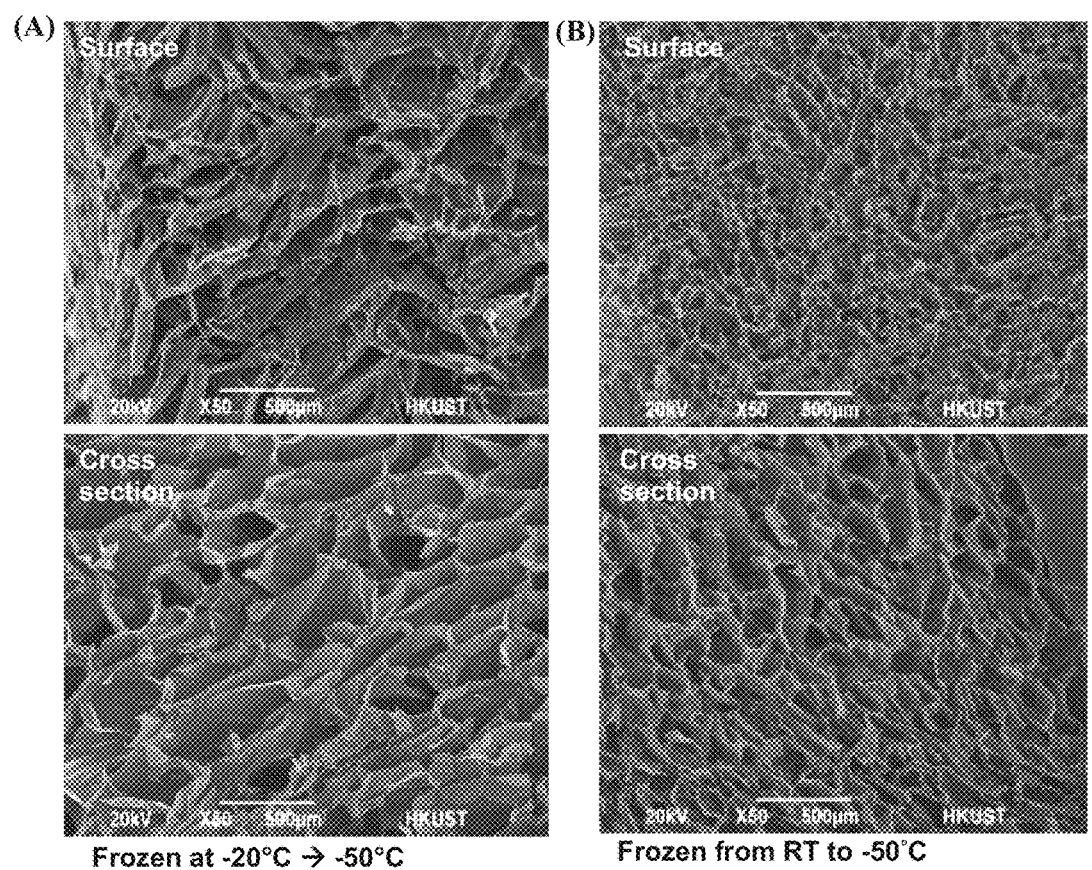
FIG. 4 shows SEM images of chitosan based filter medium prepared by different freezing profiles: (A) frozen from −20° C. to −50° C.; (B) frozen from room temperature (RT) to −50° C.; upper panel shows the surface morphology while lower panel shows the cross-sectional morphology of the filter medium.

The pore size of chitosan scaffold can also be controlled by using different freezing profiles. In one embodiment, the chitosan solution for forming the chitosan based filter medium is put into a −20° C. freezer directly and then transferred to a −50° C. freezer (Profile 1). In another embodiment, the same chitosan solution is frozen gradually from room temperature to −50° C. with the cooling rate at 1° C./min (Profile 2). The SEM images of chitosan based filter medium generated under different freezing profiles described in this example are shown in FIG. 4. The pore size of the chitosan based filter medium generated under Profile 1 (FIG. 4A) is different from that generated under Profile 2

(FIG. 4B). The average pore size of the filter medium prepared under Profile 1 is less than 100 μm while that of the filter medium prepared under Profile 2 is about 200 μm. The desired pore size of the filter medium depends on the purpose of filtration, such as the size of the materials to be filterd out from the influent, flow rate, etc. In this example, the chitosan solution contains 1.8% w/w chitosan, 0.3% acetic acid, and 0.5% TPP.

Example 5—Manipulating Pore Sizes by Using Different Crosslinking Agent

Figure 5A:
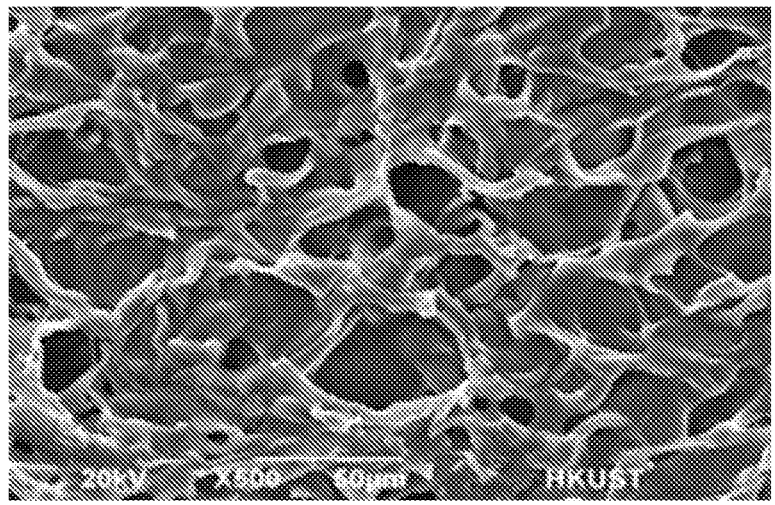
FIG. 5 shows SEM images of chitosan based filter medium prepared by different crosslinkers: (A) 0.25M TPP; (B) 0.5M NaOH.
Figure 5B:
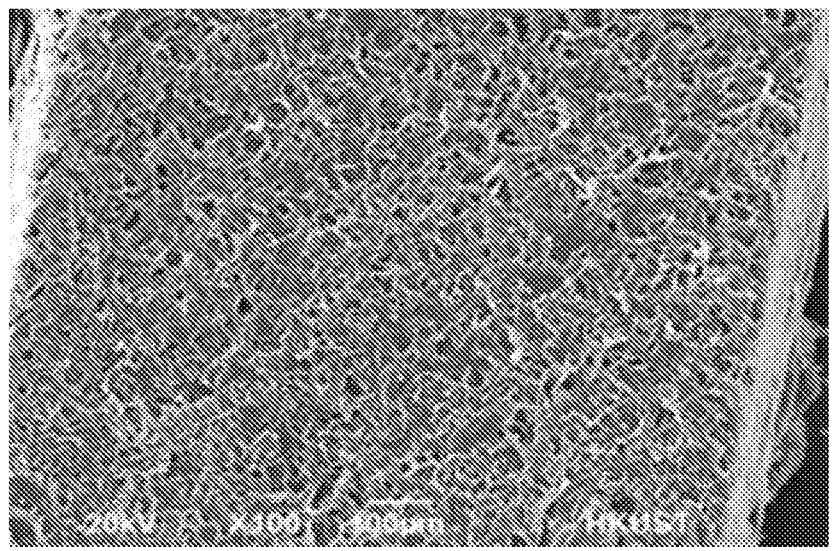

Although TPP is a typical crosslinker to crosslink the chitosan polymer, there are other types of crosslinker, such as glutaraldehyde, polyethylene glycol, and sodium hydroxide (NaOH). In this example, the morphology and pore sizes of chitosan based filter medium prepared by using TPP and sodium hydroxide are studied under SEM and compared. The SEM images show that morphology and pore size of the chitosan based filter medium crosslinked with TPP (FIG. 5A) is different from the filter medium crosslinked with NaOH (FIG. 5B). Table 3 lists out the conditions used in two different samples, labeled as sample number 1 and number 2, corresponding to FIGS. 5A and 5B, respectively.

TABLE 3

| Sample No. | Chitosan (wt %) | Cooling Method (1st) | Cooling Method (2nd) | Soaking Solvent (e.g. water) with Crosslinker |
|---|---|---|---|---|
| 1 | 2.5 | Freezer (−50° C.) | Air Dried | 0.25M TPP |
| 2 | 2.5 | Freezer (−50° C.) | Air Dried | 0.5M NaOH |

In summary, examples 1-5 demonstrate that the morphology and pore size of the chitosan scaffold can be manipulated by varying different parameters, such as crosslinking degree, the amount of copolymer added, freezing method and profile, and the type of crosslinker, etc. Overall, a desirable pore size of the present filter medium for general purpose is about 5 μm.

Example 6—Effect of Different Compositions of Chitosan/$TiO_2$ on Self-regenerating Ability of Chitosan Based Filter Medium In this example, three compositions of chitosan/$TiO_2$ are prepared to compare the effect of different proportion of chitosan and $TiO_2$ on removal percentage of organic pollutant in the influent flowing through the chitosan based filter medium. In one embodiment, a weight ratio of chitosan to TiO2 at about 1:2.78, or at about 0.18 g chitosan to about 0.5 g $TiO_2$, in 15 ml water is used to prepare the chitosan based filter medium (composition 1). Eighteen influents where each of them contains organic pollutants (e.g. allura red) at COD of 700 mg/L are used to flow through the filter medium formed by using the composition 1. The COD of the effluent is measured at each time after filtration to determine the removal percentage of the organic pollutants from the influent by the filter medium. In this embodiment, after filtering the $3^{rd}$, $4^{th}$, $5^{th}$, $6^{th}$, $9^{th}$, and $13^{th}$ influents, the filter medium prepared according to the composition 1 are treated under UV light for 3 hrs (after filtering $3^{rd}$ influent) or 6 hrs (after filtering $4^{th}$, $5^{th}$, $6^{th}$, $9^{th}$ and $13^{th}$ influents) with or without a slightly alkaline buffer (e.g. at pH 9). Table 4 shows the removal percentage of the organic pollutants from the influents being flown through the filter medium prepared according to the composition 1, which are treated under different conditions or for different volumes of the influent.

TABLE 4

| Filtration Order | Influent Volume (COD 700 mg/L organic pollutant) | Removal Percentage |
|---|---|---|
| $1^{st}$ | 5 ml | 95.10% |
| $2^{nd}$ | 10 ml | 90.15% |
| $3^{rd}$ | 5 ml | 82.19% |
| | UV (3 hrs) | |
| $4^{th}$ | 5 ml | 69.88% |
| | UV(6 hrs) | |
| $5^{th}$ | 5 ml | 79.35% |
| | UV(6 hrs) | |
| $6^{th}$ | 5 ml | 22.66% |
| | UV (6 hrs) with pH 9 buffer | |
| $7^{th}$ | 5 ml | 99.02% |
| $8^{th}$ | 5 ml | 96.59% |
| $9^{th}$ | 5 ml | 88.14% |
| | UV (6 hrs) with pH 9 buffer | |
| $10^{th}$ | 5 ml | 95.03% |
| $11^{th}$ | 5 ml | 93.62% |
| $12^{th}$ | 5 ml | 85.28% |
| $13^{th}$ | 5 ml | 78.20% |
| | UV (6 hrs) with pH 9 buffer | |
| $14^{th}$ | 5 ml | 98.25% |
| $15^{th}$ | 5 ml | 95.73% |
| $16^{th}$ | 5 ml | 94.83% |
| $17^{th}$ | 5 ml | 90.73% |
| $18^{th}$ | 10 ml | 80.92% |

Overall, the filter medium prepared according to the composition 1 has about 4 times self-regenerating ability. Self-regenerating ability in this example is defined by the number of times of regeneration activated by the UV light which can restore the same or similar level of removal percentage for the pollutants as in the preceding round of filtration. For example, if the removal efficiency of the filter medium can be restored for up to two times by exposing the same to the UV light, the self-regenerating ability will be determined as two times.

In another embodiment, a weight ratio of about 1:3.8, or 0.2 g chitosan to 0.75 g $TiO_2$, in 15 mL water is used to prepare the chitosan based filter medium (composition 2). Table 5 shows removal percentage of organic pollutants from the influent by the filter medium prepared according to the composition 2, where after filtering $6^{th}$ and $11^{th}$ influents, the filter is treated with UV for 6 hrs.

TABLE 5

| Filtration Order (5 ml of COD 700 mg/L organic pollutant) | Removal Percentage |
|---|---|
| 1 | 99.16% |
| 2 | 98.86% |
| 3 | 94.07% |
| 4 | 89.39% |
| 5 | 86.91% |
| 6 | 76.37% |
| UV (6 hrs) | |
| 7 | 90.11% |
| 8 | 92.49% |
| 9 | 86.49% |

TABLE 5-continued

| Filtration Order (5 ml of COD 700 mg/L organic pollutant) | Removal Percentage |
|---|---|
| 10 | 83.43% |
| 11 | 72.69% |
| UV (6 hrs) | |
| 12 | 76.37% |
| 13 | 61.75% |

Overall, the self-regenerating ability of the filter medium prepared according to the composition 2 is about 2 times.

In yet another embodiment, the same weight ratio of chitosan to $TiO_2$ as in composition 1 but the concentration of each component is increased by 50%, i.e. about 0.27 g chitosan and 0.75 g $TiO_2$ in 15 mL water (composition 3). The removal percentage of the organic pollutants from each influent is measured and shown in Table 6.

TABLE 6

| Filtration Order | Influent Volume (ml) | Removal Percentage (%) |
|---|---|---|
| $1^{st}$ | 10 | 99 |
| $2^{nd}$ | 5 | 99 |
| $3^{rd}$ | 10 | 99 |
| $4^{th}$ | 10 | 99 |
| $5^{th}$ | 10 | 98 |
| $6^{th}$ | 10 | 98 |
| $7^{th}$ | 10 | 97 |
| $8^{th}$ | 10 | 96 |
| $9^{th}$ | 10 | 94 |
| $10^{th}$ | 10 | 90 |
| $1^{st}$: UV irradiation (3 hrs) | | |
| $11^{th}$ | 5 | 99 |
| $12^{th}$ | 5 | 91 |
| $2^{nd}$: UV irradiation (6 hrs) | | |
| $13^{th}$ | 5 | 99 |
| $14^{th}$ | 5 | 98 |
| $15^{th}$ | 5 | 96 |
| $16^{th}$ | 5 | 91 |
| $3^{rd}$: UV irradiation (3 hrs) | | |
| $17^{th}$ | 5 | 99 |
| $18^{th}$ | 5 | 98 |
| $19^{th}$ | 5 | 91 |
| $4^{th}$: UV irradiation (3 hrs) | | |
| $20^{th}$ | 5 | 96 |
| $21^{st}$ | 5 | 73 |
| $5^{th}$: UV irradiation (3 hrs) | | |
| $22^{nd}$ | 5 | 95 |
| $23^{rd}$ | 5 | 77 |
| $6^{th}$: UV irradiation (3 hrs) | | |
| $24^{th}$ | 5 | 95 |
| $25^{th}$ | 5 | 69 |
| $7^{th}$: UV irradiation (6 hrs) | | |
| $26^{th}$ | 5 | 92 |
| $27^{th}$ | 5 | 55 |
| $8^{th}$: UV irradiation (6 hrs) | | |
| $28^{th}$ | 5 | 94 |
| $29^{th}$ | 5 | 47 |
| $9^{th}$: UV irradiation (6 hrs) | | |
| $30^{th}$ | 5 | 86 |
| $31^{st}$ | 5 | 39 |
| $10^{th}$: UV irradiation (6 hrs) | | |
| $32^{nd}$ | 5 | 95 |
| $33^{rd}$ | 5 | 39 |
| $11^{th}$: UV irradiation (6 hrs) | | |
| $34^{th}$ | 5 | 93 |

After filtering $10^{th}$, $12^{th}$, $16^{th}$, $19^{th}$, $21^{st}$, $23^{rd}$, $25^{th}$, $27^{th}$, $29^{th}$, $31^{st}$, $33^{rd}$ influents, the filter medium is treated with UV for 3 hrs or 6 hrs, treatment duration depending on the degree of accumulation of the pollutants on the filter medium. Overall, the filter medium prepared according to composition 3 has about 11 times self-regenerating ability. In this example, any of the three compositions further comprises 0.3% acetic acid and 0.5% TPP.

Figure 6:
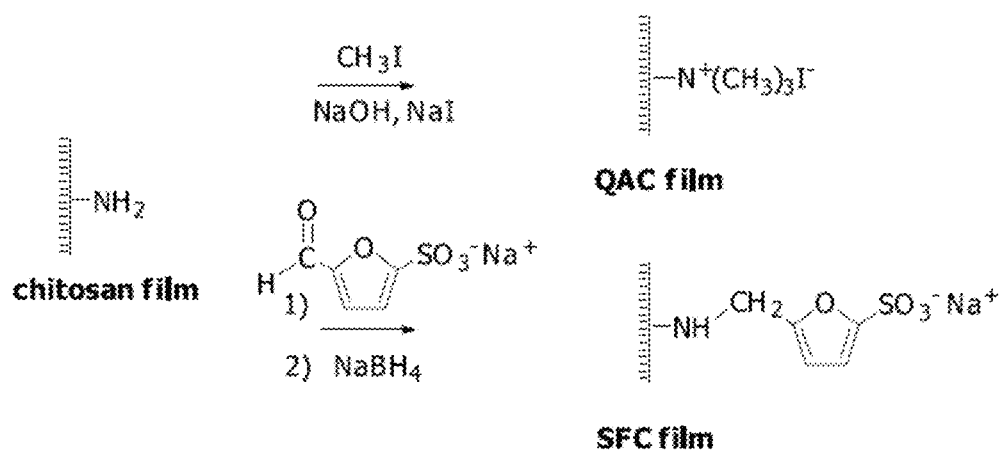
FIG. 6 is a schematic diagram showing different surface charge treatments by using different chemicals. QAC: Quaternary ammonium chitosan; SFC: N-sulfofurfuryl chitosan.

FIG. 6 depicts how the surface charge of the filter medium is tuned in order to absorb pollutants with different chargeability. For example, the chitosan based filter medium can be altered into positively charged by introducing quaternary ammonium on the surface of the filter medium through reacting the as-prepared filter medium with $CH_3I$ in the presence of NaOH or NaI. The surface of the chitosan based filter medium can also be altered into negatively charged by reacting the filter medium with 5-formyl-2-furansulfonic acid in the presence of $NaBH_4$.

Example 7—Filtration Efficiency of Present Filter Medium

A 5.0 μm polybeads solution with precise monodisperse particle size distributions is used to test the filtration efficiency of the present filter medium. The filtration efficiency is measured by filtering a certain amount of polybeads solution through the chitosan filter membrane and measuring the UV absorbance before and after filtration. The result (Table 7) shows that the filter medium can effectively filter out 95% of 5.0 μm beads.

TABLE 7

| | Polybeads size | Filtration Efficiency (%) |
|---|---|---|
| $TiO_2$/chitosan water filter | 5.0 μm | 95 |

Figure 7:
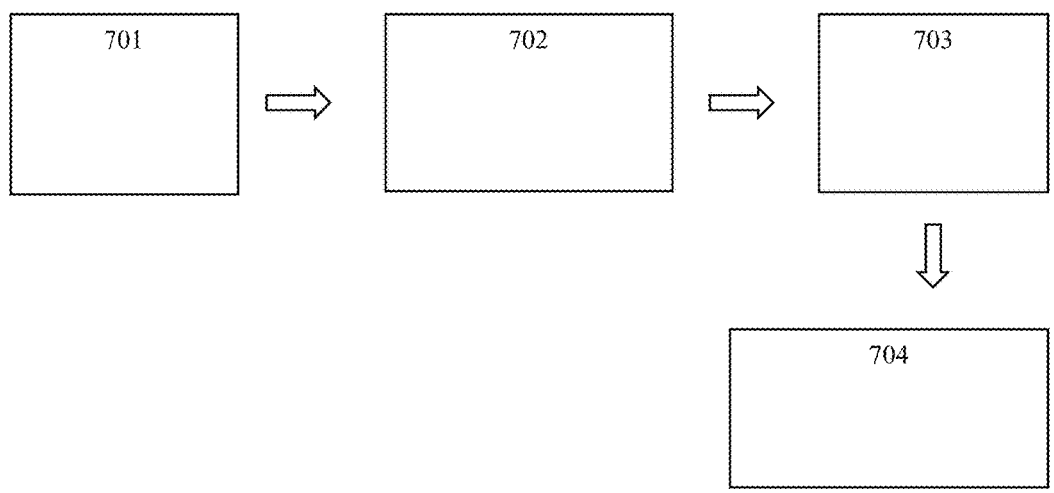
FIG. 7 is a flow chart illustrating the procedure of fabricating the filter medium of the present invention.

FIG. 7 illustrates a general fabrication procedure for the filter medium according to one of the embodiments of the present invention. Commercially available chitosan powder is dissolved into deionized water with acetic acid by stirring till a homogeneous solution is formed (701)). The stirring of mixture till homogeneous state in 701 may take about an hour. In an embodiment, 0.27 g chitosan powder is dissolved into 15 mL DI water with 0.05 mL acetic acid. Acetic acid facilitates dissolving chitosan powder into water. Nanoparticles of photocatalytic metal oxide are added into the stirring chitosan mixture until a homogeneous mixture is obtained (702). In one embodiment, 0.75 g $TiO_2$ nanoparticles are added into the stirring chitosan mixture and the mixture is stirred until it becomes homogeneous. Once the mixture from 702 becomes homogeneous, the mixture is ready for being freeze-dried. In one embodiment, about 15 g of the homogeneous mixture from 702 is poured into a 5-cm petri dish and is subject to freeze drying in a freeze dryer (703) to become a scaffold. During freeze drying, the mixture from 702 poured into the petri dish is first frozen at −55° C. for 4 hours. It is followed by 2 drying cycle process: the first drying cycle is to subject the frozen sample to −55° C. for an hour and at −10° C. for 12 hours. The second drying cycle is to subject the frozen sample obtained from the first drying cycle to air drying at 40° C. for an hour. After the freeze drying from 703, the freeze dried scaffold is soaked in a crosslinker solution containing a crosslinker (704). In one embodiment, the freeze dried chitosan scaffold is added into 20 mL 2.5 wt % Trisodium citrate dihydrate for 15 minutes.

Example 8—Bacterial Removal Efficiency of Present Filter Medium

The bacterial removal efficiency of the filter medium prepared according to the composition 3 in example 6 is measured by filtering a certain amount of *E. Coli* solution through the filter medium and the number of *E. Coli* in the filtrate is counted to compare the initial number of *E. coli* in the solution. In this example, 30 ml of *E. Coli* solution is filtered through the present filter medium and the number of *E. Coli* in the solution before and after filtration is counted. Each sample is tested in duplicate and average efficiency in terms of the removal percentage is calculated. Test result is listed in Table 8.

TABLE 8

|  | No. of *E. Coli* in the solution | Removal Efficiency | Average Efficiency |
|---|---|---|---|
| Sample 1 |  |  |  |
| Original solution | 2,520 |  |  |
| Filtrate 1 | 0 | 100.0% | 99.4% |
| Filtrate 2 | 30 | 98.8% |  |
| Sample 2 |  |  |  |
| Original solution | 360 |  |  |
| Filtrate 1 | 0 | 100.0% | 100% |
| Filtrate 2 | 0 | 100.0% |  |
| Sample 3 |  |  |  |
| Original solution | 1,440 |  |  |
| Filtrate 1 | 0 | 100.0% | 100% |
| Filtrate 2 | 0 | 100.0% |  |

Figure 8:
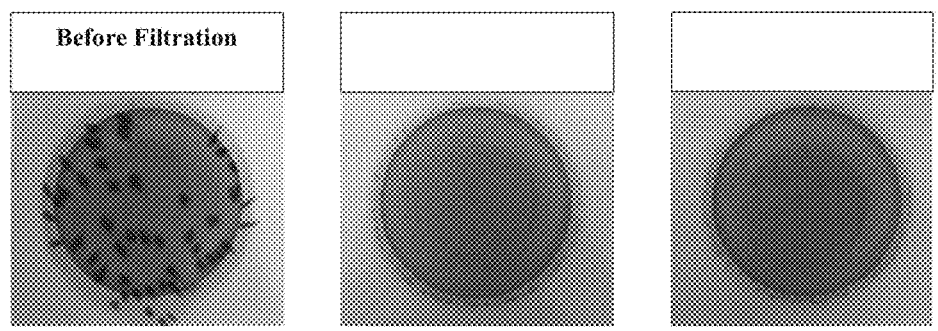
FIG. 8 shows three photos of the solution containing certain amount of bacteria (i.e. E. coli) before and after filtration through the present filter medium prepared according to an embodiment of the present invention. The left panel shows the solution containining bacteria before filtration; middle panel shows the filtrate after the first filtration; right panel shows the filtrate after the second filtration.

From Table 8, it is shown that the average bacterial removal efficiency of the present filter is about 99% or more. In FIG. 8, the three photos taken from aerial view of the solution containing the bacteria show the visual difference before filtration through the present filter medium and after two rounds of filtration through the present filter. In this figure, there are about 1,440 *E. coli* in the solution (sample 3 in this example). It is visually clear after the first filtration through the present filter medium. Second batch of bacteria-containing solution is also visually clear after the second filtration through the same filter medium. Both Table 8 and FIG. 8 support that the present filter medium is effective in filtering bacteria from the solution.

Example 9—Heavy Metal Chelating Ability of Present Filter Medium

The heavy metal chelating ability of the present filter medium is measured by filtering a certain amount of the heavy metal solution through the filter medium and measuring the amount of the heavy metal in the filtrate.

In this example, 40 ml of heavy metal solution containing Cd, Pb, and Hg are filtered through the present filter medium and the amount of each heavy metal in the solution is measured using Inductively Coupled Plasma-Optical Emission Spectrometer (ICP-OES). The result is listed in Table 9.

TABLE 9

| Heavy Metal | Influent amount (mg) | Removal weight (mg) | Absorptibility of present filter medium* (mg/g) |
|---|---|---|---|
| Cd | 27.33 | 25.44 | 98.99 |
| Pb | 20.13 | 20.08 | 78.13 |
| Hg | 62.11 | 45.11 | 175.53 |

*net weight of the present filter medium is 0.257 g

From Table 9, the absorptibility of the present filter medium for Cd is about 98.99 mg/g or more; about 78.13 mg/g or more for Pb; and about 175.53 mg/g or more for Hg. Among the three heavy metals in this example, the present filter medium is the most effective in removing Hg.

Figure 9:
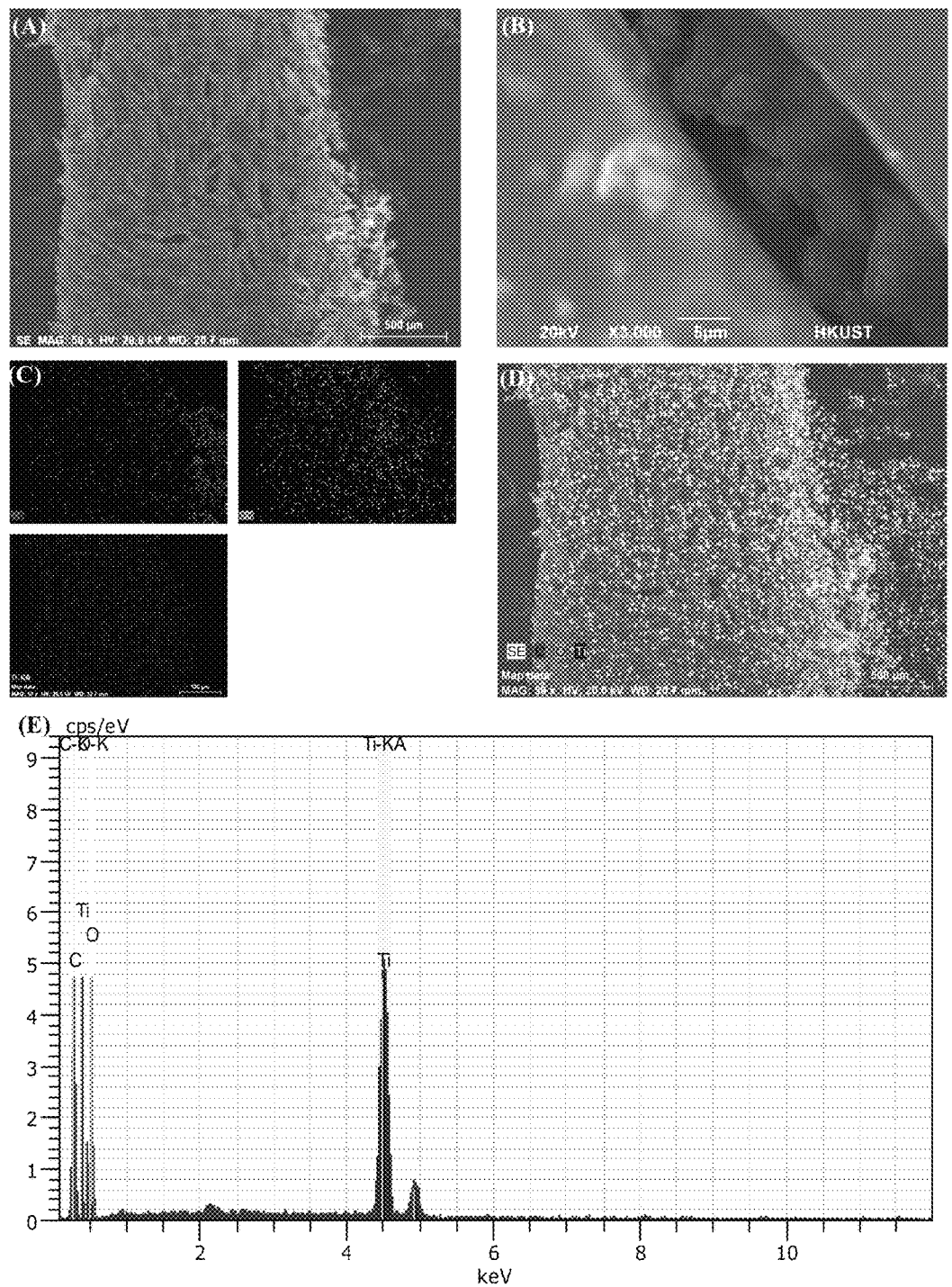
FIG. 9 shows SEM images and EDX taken from the top surface of the filter medium of the present invention: (A) SEM image, top view, 50× magnification, scale bar=100 μm; (B) SEM image, top view, 3,000× magnification, scale bar=5 μm; (C) SEM image illustrating distribution of different elements such as carbon (top left panel), oxygen (top right panel), and titanium (bottom left panel) on the top surface of the filter medium; (D) overlapping SEM images of (A) and (C) to show distribution of different elements (e.g., carbon, oxygen and titanium) on the top surface of the filter medium; (E) energy-dispersive X-ray spectroscopy (EDX) of different elements on top surface of the filter medium.
Figure 10:
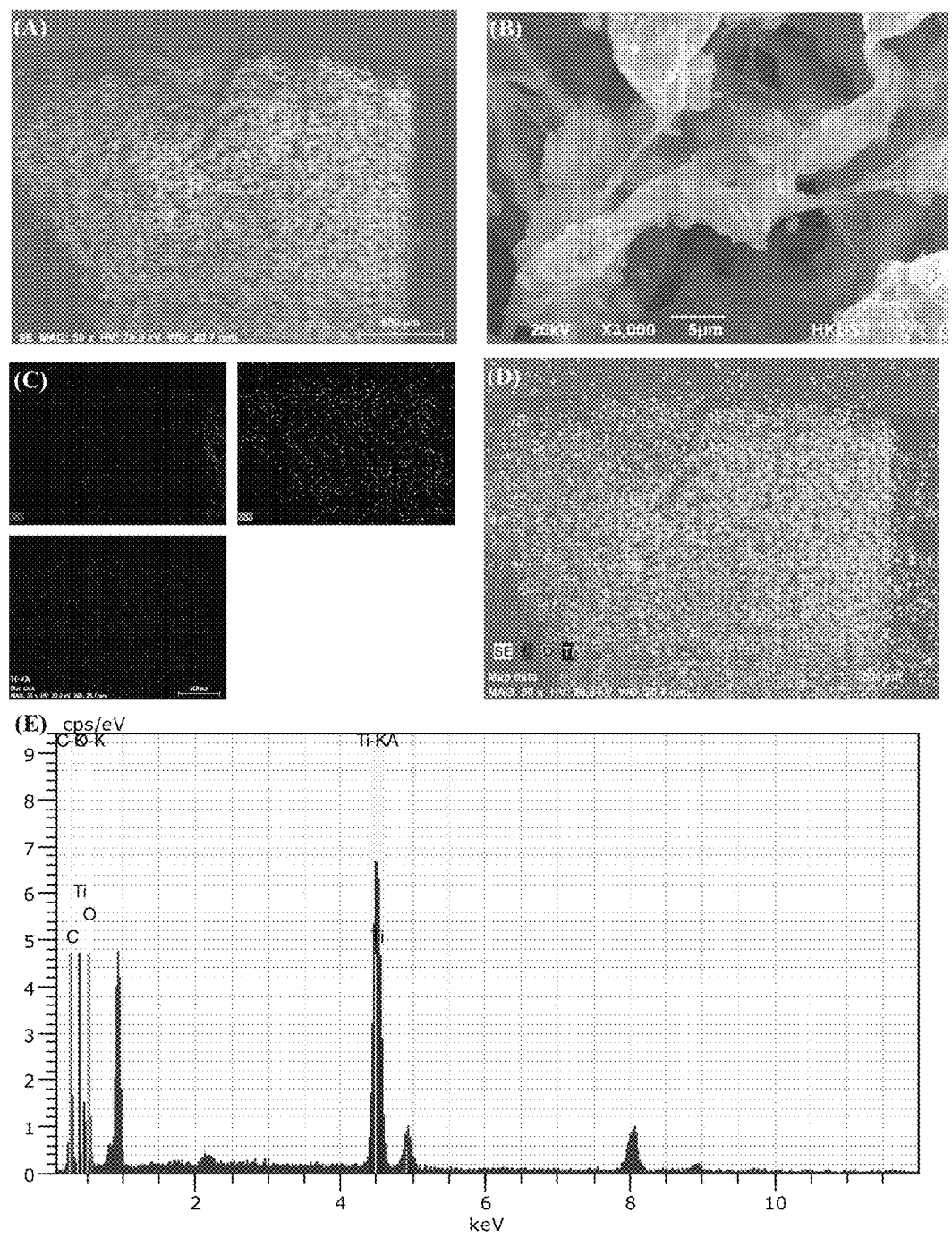
FIG. 10 shows SEM images and EDX taken from the bottom side of the filter medium of the present invention: (A) SEM image, top view, 50× magnification, scale bar=100 μm; (B) SEM image, top view, 3,000× magnification, scale bar=5 μm; (C) SEM image illustrating distribution of different elements such as carbon (top left panel), oxygen (top right panel), and titanium (bottom left panel) on the top surface of the filter medium; (D) overlapping SEM images of (A) and (C) to show distribution of different elements (e.g., carbon, oxygen and titanium) on the top surface of the filter medium; (E) energy-dispersive X-ray spectroscopy (EDX) of different elements on top surface of the filter medium.

FIGS. 9 and 10 show the morphology and distribution of different elements on both the surface and bottom of the filter medium prepared according to composition 3 in example 6. The EDX of both the surface and bottom of the filter medium demonstrates that $TiO_2$ nanoparticles are evenly dispersed on both sides of the filter medium, ensuring the self-regenerating ability of the filter medium can be fully executed when it is exposed to UV light.

INDUSTRIAL APPLICABILITY

The filter medium of the present invention is useful in water and gas filtering and disinfection.

It is understood that the method described herein may be performed in different order, concurrently and/or together with other steps not mentioned herein but readily appreciated by one skilled in the art to obtain the filter medium of the present invention. Without further elaboration, it is believed that one skilled in the art can, based on the description herein, modify the present invention without departing the spirit of the present invention and utilize the present invention to its fullest extend. All publication recited herein are hereby incorporated by reference in their entirety.

What is claimed is:

1. A method for preparing a self-regenerative gaseous and water pollutant filter membrane, said filter membrane being formed by a composition comprising chitosan derivatives or a mixture of chitosan derivatives and a polymer in a weight ratio from 1:1 to 3:1, a photocatalytic metal oxides being self-regenerative under exposure to light for a period of time, said filter membrane being prepared by selecting a specific weight ratio between said chitosan derivatives and said photocatalytic metal oxide, freezing said composition at a specific freezing temperature and profile from room temperature to from −10° C. to −55° C. at a freezing rate of about 1° C./min followed by air drying, and using a specific concentration of a crosslinker for cross-linking with the freeze-dried and air-dried composition for less than 20 minutes in order to result in a desired pore size, surface charge, at least two times of self-regenerating ability, and over 90% removal percentage of the organic pollutants from each influent flowing through said filter membrane.

2. The method of claim 1, wherein said specific weight ratio between said chitosan derivatives and said photocatalytic metal oxide is from 1:2.78 to 1:3.8.

3. The method of claim 1, wherein said composition comprises 0.27 g chitosan and 0.75 g $TiO_2$ in 15 mL water such that the self-regenerating ability of said filter membrane reaches eleven times.

4. The method of claim 1, wherein said specific concentration of said crosslinker is from 0.0136M to 0.068M.

5. The method of claim 1, wherein said polymer is selected from synthetic polymer or biopolymer.

6. The method of claim 5, wherein said synthetic polymer is copolymer comprising polyvinyl alcohol, polyethylene glycol, and polyacrylic acid.

7. The method of claim 5, wherein said biopolymer comprises cellulose, carrageenan, and alginate.

8. The method of claim 1, wherein said photocatalytic metal oxide comprises titanium dioxide, zinc oxide, vanadium oxide, and manganese dioxide, which is in particle form with a particle size ranging from 10 nm to 10 μm.

9. The method of claim 1, wherein said crosslinker comprises Trisodium citrate dihydrate, sodium hydroxide, tripolyphosphate (TPP), glyoxal, glutaraldehyde, polyethylene glycol, epichlorohydrin, N-hydroxysuccinimide, 1-ethyl-3-(3-dimethylaminopropyl) carbodiimide, 1,4 butanediol diglycidyl ether, formaldehyde, genipin, and oxalic acid.

10. The method of claim 9, wherein said chitosan is crosslinked by said crosslinker ranging from 0.0136M to 0.068M to result in a pore size of said filter membrane ranging from 100 nm to 100 μm.

11. The method of claim 10, wherein said crosslinker is tripolyphosphate in a concentration of 0.5 wt % while the weight percentage of said chitosan is 2.5 wt % in said composition to be frozen.

12. The method of claim 1, wherein said polymer is in a concentration from 0.24 wt % to 0.50 wt % in said composition.

13. The method of claim 1, wherein said photocatalytic metal oxides is self-regenerated when said filter membrane is exposed to ultra-violet light for at least 3 hours.

14. The method of claim 1, wherein the surface charge of said filter membrane is tuned to positive charge by introducing quaternary ammonium to said surface.

15. The method of claim 1, wherein the surface charge of said filter membrane is tuned to negative charge by introducing 5-formyl-2-furansulfonic acid to said surface.

16. The method of claim 1, wherein the surface charge of said filter membrane is neutralized by sodium hydroxide.

17. The method of claim 1, wherein said method comprising the following steps:
(a) dissolving chitosan powder and said polymer into deionized water with acetic acid or providing a mixture of said chitosan derivatives and said polymer in a weight ratio from 1:1 to 3:1 followed by adding said photocatalytic metal oxide to form a mixture, and stirring the mixture for about an hour until homogeneous;
(b) freezing drying the homogeneous mixture obtained from (a) at about −55° C. for about 4 hours, followed by a two drying cycle treatment including a first drying cycle of −55° C. for about an hour and subsequently at −10° C. for about 12 hours, and a second drying cycle of about 40° C. for about an hour to obtain a scaffold;
(c) soaking the scaffold obtained from (b) into a crosslinking agent containing said crosslinker to crosslink the chitosan; and
(d) optionally tuning the surface charge of the filter membrane by treating the surface of the chitosan scaffold with an acid or an alkaline.

18. A chitosan-based filter medium prepared by the method of claim 1.

* * * * *